(12) United States Patent
Knepp et al.

(10) Patent No.: US 6,264,990 B1
(45) Date of Patent: Jul. 24, 2001

(54) STABLE PROTEIN AND NUCLEIC ACID FORMULATIONS USING NON-AQUEOUS, ANHYDROUS, APROTIC, HYDROPHOBIC, NON-POLAR VEHICLES WITH LOW REACTIVITY.

(75) Inventors: Victoria Marie Knepp, Ridgefield, CT (US); Steven Joseph Prestrelski, Mt. View, CA (US); Jessica G. Smith, Sunnyvale, CA (US); Manley T. Huang, Palo Alto, CA (US)

(73) Assignee: ALZA Corporation, Mountain View, CA (US)

( * ) Notice: Subject to any disclaimer, the term of this patent is extended or adjusted under 35 U.S.C. 154(b) by 0 days.

(21) Appl. No.: 09/269,685

(22) PCT Filed: Oct. 15, 1997

(86) PCT No.: PCT/US97/18575

§ 371 Date: Dec. 14, 1999

§ 102(e) Date: Dec. 14, 1999

(87) PCT Pub. No.: WO98/16250

PCT Pub. Date: Apr. 23, 1998

Related U.S. Application Data

(60) Provisional application No. 60/052,920, filed on Jul. 15, 1997, and provisional application No. 60/028,167, filed on Oct. 16, 1996.

(51) Int. Cl.$^7$ .............................. A61K 9/50; A61K 9/14; A61K 38/00
(52) U.S. Cl. .............................. 424/499; 424/489; 514/2
(58) Field of Search ...................................... 424/422, 423, 424/489, 499; 435/320.1; 514/44, 832, 834, 2

(56) References Cited

U.S. PATENT DOCUMENTS 5,480,914   1/1996  Meadows ............................. 514/743
5,518,731 * 5/1996  Meadows ............................. 424/427

FOREIGN PATENT DOCUMENTS 0 177 342 A2    4/1986   (EP) .
0 427 998 A2    5/1991   (EP) .
2 34 2073 A1    9/1977   (FR) .
WO 93/24640    12/1993   (WO) .
WO 93/25673    12/1993   (WO) .
WO 94/06452     3/1994   (WO) .
WO 96/27393     9/1996   (WO) .
WO 96/41873    12/1996   (WO) .

OTHER PUBLICATIONS

Knepp et al. Pharmaceutical Research. 15(7): 10901095 1998.*
Branch, A.D. TIBS. 23: 45–50, Feb. 1998.*
Ledley, F.D. Pharmaceutical Research. 13:1595–1614, Nov. 1996.*
Verma et al. Nature. 389: 239–242, 1998.*
Wang et al., 1998, J. Parenteral Science & Technology 42: S4–S26.
Deetz et al., 1988, Trends in Biotechnol. 6: 15–19.
Chin et al., 1994, Biotechnol. Bioeng. 44: 140–145.
Klibanov, 1989, TIBS 14: 141–144.
Zaks et al., 1984, Science 224: 1249–1251.
Affleck et al., 1992, Proc. Natl. Acad. Sci. USA 89: 1100–1104.
Zaks et al., 1998, J. Biol. Chem. 263: 8017–8021.
Guagliardi et al., 1989, Chimicaoggi 31–36.
Paulitis et al., 1992, Annals New York Acad. Sci. 672: 278–282.
Matsuura et al., 1993, J. Amer. Chem. Soc. 115: 12261–1264.
Prestrelski et al., 1993, Biophys. J. 65: 661–671.
Volkin et al., 1991, Biotechnol. Bioeng. 37: 843–853.
Aldercreutz et al., 1987, Biocaatalysis 1: 99–108.
Guinn et al., 1991, Biotechnol. Bioeng. 37: 303–308.
Desai et al., 1995, J. Am. Chem. Soc. 117: 3940–3945.
Yu et al., 1996, J. Pharm. Sci. 85: 396–401.
Burke et al, 1989, J. Am. Chem. Soc. 111: 8290–8291.
Kanerva et al., 1989, J. Am. Chem. Soc. 111: 6865–6866.
Desai et al., 1994, J. Am. Chem. Soc. 116: 9420–9422.
Chang et al., Jan. 1996, Pharm. Tech. 80–84.
Manning et al., 1989, Pharm. Res. 6: 903–918.
Hageman, 1988, Drug Dev. Ind. Pharm. 14: 2047–2070.
Bell et al., 1995, Biopolymers 35: 201–209.
Sullivan, 1996, BioPharm Sep.: 50–51 and 65–66.
Hofland et al., 1996, Proc. Natl. Acad. Sci. 93: 7305–7309.
Ciccarone et al., 1997, lifetech.com/focus/173103.
Lifetech.com/cgi–online/techonline/document 24well May 19, 1997.
Lifetech.com/cgi–online/techonline/document May 19, 1997.
Zaks et al., 1988, J. Biol. Chem. 263: (7)3194–3201.
Zhang et al., 1995, Pharm. Res. 12: (10)1447–1452.
S.J. Singer, 1962, Advances in Protein Chemistry 17:1–68.
Huang et al., 1990, Nucleic Acids Res. 18:(4) 937–947.

* cited by examiner

Primary Examiner—Daug Trong Nguyen
(74) Attorney, Agent, or Firm—Pauline A. Clarke; Steven F. Stone

(57) ABSTRACT

This invention relates to stable non-aqueous formulations which are suspensions of proteinaceous substances or nucleic acids in non-aqueous, anhydrous, aprotic, hydrophobic, non-polar vehicles with low reactivity. More specifically, the present invention relates to stable protein or nucleic acid formulations wherein the compound remains in stable, dry powder form, yet the formulation is flowable and, therefore amenable to delivery to an animal via injection, transdermal administration, oral delivery or using an implantable device for sustained delivery. These stable formulations may be stored at elevated temperatures (e.g., 37° C.) for long periods of time and are especially useful as flowable formulations which can be shipped and/or stored at high temperatures or in implantable delivery devices for long term delivery (e.g., 1–12 months or longer) of drug.

12 Claims, No Drawings

STABLE PROTEIN AND NUCLEIC ACID FORMULATIONS USING NON-AQUEOUS, ANHYDROUS, APROTIC, HYDROPHOBIC, NON-POLAR VEHICLES WITH LOW REACTIVITY.

This application is a national stage application based on PCT Ser. No. US97/18575 filed Oct. 15,1997 which claims priority from U.S. Ser. No. 60/028,167 filed Oct. 16,1996 and U.S. Ser. No. 60/052,920 filed Jul. 15,1997.

BACKGROUND OF THE INVENTION

References

The following references are referred to by numbers in brackets ([ ]) at the relevant portion of the specification.
1. Ahern and Manning, Eds., Stability of Protein Pharmaceuticals, A: Chemical and Physical Pathways of Protein Degradation, Plenum Press, New York, 1992.
2. Wang et al., 1 988, J. Parenteral Science and Technology 42: S4-S26
3. Deetz et al., 1988, Trends in Biotechnol. 6: 15–19
4. Chin et al., 1994, Biotechnol. Bioeng. 44: 140–145
5. Klibanov, 1989, TIBS 14: 141–144
6. Zaks et al., 1984, Science 224:1249–1251
7. Affleck et al., 1992, Proc. Natl. Acad. Sci. USA 89:1100–1104
8. Zaks et al., 1988, J. Biol. Chem. 263:8017–8021
9. Volkin et al., 1991, Biotechnol. Bioeng. 37: 843–853
10. Guagliardi et al., 1989, Chimicaoggi 31–36
11. Paulaitis et al., 1992, Annals New York Acad. Sci. 672:278–282
12. Matsuura et al., 1993, J. Amer. Chem. Soc. 115:1261–1264
13. Zaks et al., 1988, J. Biol. Chem. 263:3194–3201
14. Prestrelski et al., 1993, Biophys. J. 65:661–671
15. Zhang et al., 1995, Pharm. Res. 12, 1447–1452
16. Singer et al., 1962, Adv. Prot. Chem. 1–68 entitled The Properties of Protein in Nonaqueous Solvents
17. Volkin et al., 1991, Biotechnol. Bioeng. 37: 843–853
18. Aldercreutz et al., 1987, Biocatalysis 1: 99–108
19. Guinn et al., 1991, Biotechnol. Bioeng. 37: 303–308
20. Desai et al. 1995, J. Am. Chem. Soc. 117: 3940–3945
21. Yu et al., 1996, J. Pharm. Sci. 85: 396–401
22. Burke et al., 1989, J. Am. Chem. Soc. 111: 8290–8291
23. Kanerva et al., 1989, J. Am. Chem. Soc. 111: 6865–6866
24. Desai et al., 1994, J. Am. Chem. Soc. 116:9420–9422
25. Chang et al., January 1996, Pharm. Tech. 80–84
26. Manning et al., 1989, Pharm. Res. 6: 903–918
27. Hageman, 1988, Drug Dev. Ind. Pharm. 14:2047–2070
28. Bell et al., 1995, Biopolymers 35: 201–209
29. Meadows, 1996, U.S. Pat. No. 5,480,914
30. Meadows, 1996, U.S. Pat. No. 5,518,731
31. Hageman, 1994, International Publication No. WO 94/06452
32. Hofland et al., 1996, Proc. Natl. Acad. Sci. 93:7305–7309
33. Sullivan, 1996, BioPharm September: 50–51 and 65–66.
34. Huang et al., 1996, International Publication No. WO 96/27393.
35. Debs et al., 1993, International Publication No. WO 93/25673.
36. Lemoine and Cooper, Ed., Gene Therapy, Bios Scientific Publishers, Oxford, UK, 1996.
37. Debs et al., 1993, International Publication No. WO 93/24640.
38. Gibco technical report.
39. Boehringer Mannheim technical report.
40. Avanti polar lipid technical report.
41. Szoka et al., 1996, International Publication No. WO 96/41873.
42. Huang et al., 1990, Nucl. Acids Res. 18(4): 937–947.

The disclosure of each of the above publications, patents or patent applications is hereby incorporated by reference in its entirety to the same extent as if the language of each individual publication, patent and patent application were specifically and individually incorporated by reference.

BACKGROUND OF THE INVENTION

Peptides, polypeptides, proteins and other proteinaceous substances (e.g., viruses, antibodies), collectively referred to herein as proteins, have great utility as pharmaceuticals in the prevention, treatment and diagnosis of disease. Proteins are naturally active in aqueous environments, thus the preferred formulations of proteins have been in aqueous solutions. However, proteins are only marginally stable in aqueous solutions. Thus, protein pharmaceuticals often require refrigeration or have short shelf-lives under ambient conditions. Further, many proteins have only limited solubility in aqueous solutions. Even when they are soluble at high concentrations, they are prone to aggregation and precipitation.

Proteins can degrade via a number of chemical mechanisms, including deamidation of asparagine and glutamine; oxidation of methionine and, to a lesser degree, tryptophan, tyrosine and histidine; hydrolysis of peptide bonds; disulfide interchange; and racemization of chiral amino acid residues [1, 2 and 24–28]. Water is a reactant in nearly all of these degradation pathways. Further, water acts as a plasticizer which facilitates unfolding and irreversible aggregation of proteins. Since water is a participant in almost all protein degradation pathways, reduction of the aqueous protein solution to a dry powder provides an alternative formulation methodology to enhance the stability of protein pharmaceuticals. Proteins can be dried using various techniques, including freeze-drying, spray-drying and dessication. Aqueous solutions of proteins are thus dried and stored as dry powders until their use is required.

A serious drawback to drying of proteins is that often one would like to use proteins in some sort of liquid form. Parenteral injection and the use of drug delivery devices for sustained delivery of drug are two examples of applications where one would like to use proteins in a liquid form. For injection, dried proteins must be reconstituted, adding additional steps which are time-consuming and where contamination may occur, and exposing the protein to potentially destabilizing conditions [15].

The sustained parenteral delivery of drugs, in particular proteins and nucleic acids, provides many advantages. The use of implantable devices for sustained delivery of a wide variety of drugs or other beneficial agents is well known in the art. Typical devices are described, for example, in U.S. Pat. Nos. 5,034,229; 5,057,318; and 5,110,596. The disclosure of each of these patents is incorporated herein by reference.

Proteins are only marginally soluble in non-aqueous solvents, and such solvents typically unfold and denature proteins [4, 16]. Solubilization of native proteins in non-aqueous solvents typically requires derivatization or complexation of the protein [12]. In attempting to achieve enzymatic catalysis in organic media, Klibanov and others have shown that certain catalytic enzymes can be suspended in non-aqueous vehicles as powders, typically in hydrophilic organic solvents including alcohol ketones and esters [3, 5–11, 13 and 18–23]. With enzyme hydration levels ≧10% and/or the addition of low molecular weight protic compounds, these enzymes can have enough conformational mobility to exhibit appreciable enzymatic activity. Optimal activity levels are apparently achieved at enzyme hydration of approximately 30%. At a minimum, such enzymatic activity requires a level of "essential water" hydrating the protein. However, hydration levels (generally 10–40% w/w water/protein) and/or protic solvents, such as those used in these studies, typically result in unacceptable stability of proteins for pharmaceutical purposes. A further requirement for catalysis in non-aqueous solvents is that the enzyme be dried from a solution having a pH near the optimal pH for the enzymatic activity. This pH limitation is detrimental to storage of protein pharmaceuticals, because most protein degradation mechanisms are pH dependent, and it is often the case that proteins are most stable when dried at pH values far from the value where they exhibit bioactivity [1]. Further, such catalytic enzyme systems are not amenable to the addition of protein stabilizers, particularly those that function by hydrogen bonding to the protein and reducing enzyme hydration (e.g., carbohydrates) [14].

The use of perfluorocarbons as components of drug delivery vehicles for certain ophthalmic compositions has been disclosed [29, 30]. Similarly, suspensions of growth hormone in triacetin or polyethylene glycol has been published [31].

The field of gene therapy or gene transfer is advancing both experimentally and clinically. Nucleic acids have been transferred into cells using viral vectors such as adenovirus, retrovirus, adeno-associated virus, vaccinia virus, and sindbis virus, among others. Non-viral methods have also been used, including calcium phosphate precipitation, DEAE dextran, injection of naked DNA, electroporation, cochleates, cationic lipid complexes, liposomes, polymers (such as dendrimers and PLGA), virosomes, and the like.

DNA complexed with cationic lipids and/or liposomes has been shown to be an efficient means of transfecting a variety of mammalian cells. Such complexes are simple to prepare and may be used with a wide variety of DNA's and RNA's with little restriction to the size of nucleic acid. They have the ability to transfect many different cell types with efficiency and are not immunogenic [32, 33, 35, 36]. Current nucleic acid formulations, including DNA/liposome and RNA/liposome complexes, must be mixed shortly before administration, resulting in inconvenience in manufacture, shipping, storage and administration [35, 37–40]. Frequently, these two-part formulations are not very highly concentrated, requiring the administration of large volumes of solution. Dry powder formulations containing lyophilized nucleic acid/liposome complexes have also been used [34, 41], but they require reconstitution with suitable aqueous solution just prior to administration. Aqueous complexes are inherently unstable and lose most, if not all, of their transfection activity within hours or a few days [41].

Consequently, there is a need for pharmaceutical compositions that can overcome these limitations of the prior art. Such a composition should maintain the stability of the active compound, preferably at both room and body temperature (25 and 37° C.), and exist in at least a flowable state for injection, incorporation into delivery systems designed for immediate, delayed, or long term administration or other means of administration.

SUMMARY OF THE INVENTION

The present invention provides stable non-aqueous formulations which are suspensions of peptides, polypeptides, proteins and other proteinaceous substances ("proteins" or "proteinaceous substances") or DNA- and RNA-containing compositions ("nucleic acids") in anhydrous, aprotic, hydrophobic, non-polar vehicles with low reactivity. More specifically, the present invention relates to stable formulations wherein the proteinaceous substance or nucleic acid remains in stable, dry powder form, yet the formulation is flowable and, therefore amenable to delivery to an animal via, for example, injection, ambulatory infusion or an implantable device for sustained delivery. These stable formulations may be stored at elevated temperatures (e.g., 37° C.) for long periods of time and are especially useful as flowable formulations which can be shipped and/or stored at high temperatures or in implantable delivery devices for long term delivery (e.g., 1–12 months or longer) of drug.

In one aspect, the invention provides stable protein compositions comprising a proteinaceous powder wherein the protein hydration in said powder is less than about 10%; and at least one anhydrous, aprotic, hydrophobic, non-polar, low-reactivity vehicle. In a preferred embodiment, up to about 30% (w/w) proteinaceous powder may be used in these flowable compositions.

In another aspect, the invention provides methods for preparing stable protein compositions, said methods comprising suspending a proteinaceous powder with protein hydration less than about 10% in at least one anhydrous, aprotic, hydrophobic, non-polar, low-reactivity vehicle.

In a further aspect, the invention provides methods for treating a subject suffering from or susceptible to a condition which may be alleviated or prevented by administration of a proteinaceous compound, said methods comprising administering to said subject an effective amount of a stable protein composition comprising a proteinaceous powder wherein the protein hydration in said powder is less than about 10%; and at least one anhydrous, non-polar, aprotic, hydrophobic, low-reactivity vehicle.

In yet a further aspect, the invention provides stable nucleic acid compositions comprising a nucleic acid-containing powder wherein the nucleic acid hydration in said powder is less than about 10%; and at least one anhydrous, non-polar, aprotic, hydrophobic, low-reactivity vehicle.

In yet still another aspect, the invention provides methods for preparing stable nucleic acid compositions, said methods comprising suspending a nucleic acid-containing powder with nucleic acid hydration less than about 10% in at least one anhydrous, non-polar, aprotic, hydrophobic, low-reactivity vehicle.

In yet still a further aspect, the invention provides methods for treating a subject suffering from or susceptible to a condition which may be alleviated or prevented by administration of a nucleic acid-containing compound, said methods comprising administering to said subject an effective amount of a stable nucleic acid composition comprising a nucleic acid-containing powder wherein the nucleic acid hydration in said powder is less than about 10%; and at least one anhydrous, non-polar, aprotic, hydrophobic, low-reactivity vehicle.

DETAILED DESCRIPTION OF THE INVENTION

The present invention is drawn to the unexpected discovery that suspending dry protein- or nucleic acid-containing particles in anhydrous, aprotic, hydrophobic, non-polar vehicles of low reactivity results in stable flowable non-aqueous formulations. Previously known formulations of proteinaceous compounds, which are dilute buffered aqueous solutions containing excipients such as EDTA or polysorbate 80 which must be stored at low temperatures (4–25° C.), or lyophilized powders or particles which must often be stored at low temperature and must then be reconstituted before administration, form degradation products using degradation pathways such as acid/base catalyzed hydrolysis, deamidation, racemization and oxidation. Similarly, previously known formulations of nucleic acids, even those prepared from lyophilized powders, are administered as dilute aqueous solutions which are not stable for long periods of time and which must be stored at low temperatures. In contrast, the presently claimed formulations stabilize proteins and nucleic acid compounds at elevated temperatures (e.g., 37° C.) and at high concentrations (i.e., up to about 30%). Standard peptide and protein formulations consist of dilute aqueous solutions. Drug stability is usually achieved by varying one or more of the following: pH, buffer type, ionic strength, excipients (EDTA, polysorbate 80, etc). For these formulations, degradation pathways requiring water (hydrolysis, deamidation, racemization) cannot be fully stabilized. In contrast, in the present invention, proteinaceous compounds formulated in non-aqueous, anhydrous, aprotic, hydrophobic, non-polar vehicles with low-reactivity, such as mineral oil (MO), perfluorodecalin (PFD), methoxyflurane (MF), perfluorotributylamine (PTA) and tetradecane (TD), were shown to be chemically and physically more stable than those formulated in aqueous solution. MO, PFD, MF, PTA and TD are considered anhydrous, aprotic, hydrophobic, non-polar vehicles of low reactivity. Such vehicles decrease the rate of degradation since they isolate the proteinaceous compounds from water and they lack the ability to contribute protons or other reactive moieties to degradation reactions.

The invention consists of using anhydrous, aprotic, non-polar, hydrophobic vehicles with low reactivity such as MO, PFD, MF, PTA or TD to stabilize protein formulations against both chemical and physical degradation. The discovery consists of the realization that use of MO, PFD, MF, PTA or TD improves the overall stability of proteins in a wide range of formulation conditions, including high concentrations and elevated temperatures, thus making possible shipping and/or storage of protein formulations at ambient temperature and the delivery of proteins in long term implantable devices that would not otherwise be feasible. The present invention provides flowable pharmaceutical formulations of proteinaceous substances that exhibit the requisite protein stability. These non-aqueous formulations comprise two components: 1) a protein in a stabilized powder formulation of low protein hydration; and 2) an anhydrous, hydrophobic, aprotic, non-polar vehicle of low reactivity and solubility power towards protein compounds. Optionally, the dry powder form of the protein may contain stabilizers and other excipients. Such stabilizers and excipients are those that further reduce protein hydration or protect from interfacial tension or other dehydration process-specific destabilization known to those skilled in the art.

Among other factors, it has been surprisingly discovered that when dispersed in certain vehicles, protein powders can display significantly greater stability than that observed for the dry powder alone. Such vehicles include long-chain alkanes, most preferably perfluorinated forms of alkanes. The present invention is especially advantageous because it provides the capacity to store proteins under ambient conditions for extended periods or to deliver proteins from implantable pumps for extended durations.

Lipid/DNA and lipid/RNA complexes facilitate nucleic acid uptake into cells both in vitro and in vivo. However, such complexes are inherently unstable in solution, losing most, if not all, of their activity after only a few days at ambient temperatures. This feature severely limits their applicability for use in such devices as implantable pumps, depot injection or other sustained release delivery systems where prolonged residence at 37° C. is needed. Lyophilization of these complexes results in more stable compositions, but such powders require reconstitution prior to administration to render them flowable, and the reconstituted solutions are not stable. The present invention provides flowable pharmaceutical formulations of nucleic acids that exhibit the requisite stability. These non-aqueous formulations comprise two components: 1) a nucleic acid in a stabilized powder formulation of low hydration; and 2) an anhydrous, hydrophobic, aprotic, non-polar vehicle of low reactivity and solubility power towards nucleic acids. Optionally, the dry powder form of the nucleic acid may contain the nucleic acid in the form of lipid/DNA complexes, liposomes, ribozymes, viral vectors, virosomes, dendrimers, cationic polymers, PLGA particles or the like, and/or may optionally contain stabilizers and other excipients. Such stabilizers and excipients are those that further reduce hydration or protect from interfacial tension or other process-specific destabilization known to those skilled in the art.

The formulations of the present invention are useful in a variety of delivery systems, including, but not limited to, various pumping devices (syringes, infusion sets, syringe pumps, implantable pumps, etc.), transdermal reservoir systems, liquid fill capsules, injectable depot compositions and the like. An additional advantage of the present invention over the prior art is that the formulations of the present invention prevent back diffusion of water vapor (and subsequent hydrolytic degradation) because the hydrophobic vehicle of the formulation acts as a barrier to water vapor. This is especially important when the formulations are used in implantable devices which must remain in an aqueous environment at elevated temperatures for long periods of time.

A further advantage of the present invention is that it allows for the formulation of proteins or nucleic acids in a flowable state at extremely high concentrations (up to about 30% w/w). Because the protein or nucleic acid is in a dry state, it is not subject to the degradation processes (e.g., aggregation, precipitation or fragmentation) observed for high concentration aqueous solutions.

A. Definitions:

As used herein, the following terms have the following meanings:

The term "chemical stability" means that an acceptable percentage of degradation products produced by chemical pathways such as oxidation, hydrolysis or enzymatic action is formed and/or that acceptable biological activity is retained. In particular, a formulation is considered chemically stable if no more than about 40% breakdown products are formed and/or at least 40% biological activity is retained after one week at 37° C.

The term "physical stability" means that an acceptable percentage of aggregates (e.g., dimers, trimers and larger forms) and/or cleavage products is formed. In particular, a formulation is considered physically stable if no more that about 10% aggregates and/or clevage products are formed after one week at 37° C.

The term "stable formulation" means that at least about 50% chemically and physically stable protein or nucleic acid compound remains after one week at 37° C. Particularly preferred formulations are those which retain at least about 65%, and most particularly, at least about 80% chemically and physically stable compound under these conditions. Especially preferred stable formulations include those which remain flowable at high protein or nucleic acid loading (e.g., at or above 1%).

The terms "protein" and/or "proteinaceous compound" and/or "proteinaceous substance" mean peptides, polypeptides, proteins, viruses, antibodies, etc. which comprise polymers of amino acid residues bound together by amide (CONH) linkages. Both naturally-derived or purified and recombinantly produced moieties are included in these terms. These terms also include lipoproteins and post-translationally modified forms, e.g., glycosylated proteins. Analogs, derivatives, agonists, antagonists and pharmaceutically acceptable salts of any of these are included in these terms. The terms also include proteins and/or protein compounds and/or protein substances which have D-amino acids, modified, derivatized or non-naturally occurring amino acids in the D- or L-configuration and/or peptomimetic units as part of their structure.

The term "excipient" means a more or less inert component which is added to the finished formulation other than the therapeutic ingredient.

The term "non-polar vehicle" means a vehicle which has a dielectric constant of less than or equal to about 15.

The term "aprotic vehicle" means a vehicle which does not contain acidic hydrogen (i.e., a hydrogen attached to an oxygen or nitrogen). The term "anhydrous vehicle" means a vehicle which does not contain water, including water adsorbed on its surface or combined as water of crystallization.

The terms "vehicle with low reactivity" and/or "low-reactivity vehicle" mean a vehicle which generally does not solubilize or otherwise react with proteinaceous compounds and/or nucleic acids. Low-reactivity vehicles are non-polar and have a Hildebrandt number of less than about 8.0. Examples of vehicles with low reactivity include: a) saturated hydrocarbons, b) halogenated saturated or unsaturated hydrocarbons, and c) esters and ethers of a) or b).

The terms "proteinaceous particle" and/or "proteinaceous powder" mean particles which contain proteins, proteinaceous compounds or proteinaceous substances. The proteinaceous particles of the present invention may, optionally, contain excipients, as defined above. Such excipients may include carbohydrates, non-ionic surfactants, buffers, salts, carrier proteins, preservatives and the like. However, the proteinaceous powders of the present invention do not contain polymers, nor are they encapsulated by polymeric materials (i.e., they are not microparticles or microcapsules as defined, for example, in U.S. Pat. No. 5,518,731).

The term "hydration" means water molecules associated with either the protein or nucleic acid, excipients or carriers.

The term "hydrophobic" means incapable of dissolving to any appreciable extent in water.

The term "nucleic acid" means unbranched (linear or circular) chains of nucleotides in which the 5' phosphoric group of each nucleotide is esterified with the 3' hydroxyl of the adjoining nucleotide. The term includes ribonucleic acid (RNA) and deoxyribonucleic acid (DNA) constructs. The term nucleic acid includes single and double stranded molecules, oligonucleotides, gene expression constructs, mRNA molecules, ribozymes, and the like. Naturally-derived or purified, synthetically produced and recombinantly produced moieties are all included in the term. The term also includes analogs, derivatives, and constructs that include promoter, leader, signal, polyadenylation or intron sequences, locus control regions, markers, and the like. Nucleic acids containing modified, derivatized or non-naturally occurring nucleotide units as part of their structure are also included in the term.

The terms "lipid/DNA complex" and "lipid/RNA complex" mean complexes that form between nucleic acids and small, cationic unilamellar vesicles held together by electrostatic interactions rather than by encapsulation of the nucleic acids in liposomes. A variety of topological arrangements can occur, such as DNA condensation, liposome aggregation and fusion.

The term "liposome" means the multi- or unilamellar vesicles formed from phospholipids which are used as carriers for drugs and macromolecules, especially nucleic acids.

The terms "nucleic acid particle" and/or "nucleic acid powder" mean particles which contain DNA or RNA. The nucleic acid may optionally be complexed with lipids or in liposomes, ribozymes, viral vectors, virosomes, dendrimers, cationic polymers, PLGA particles, or the like. The nucleic acid particles of the present invention may, optionally, contain excipients, as defined above. Such excipients may include carbohydrates, non-ionic surfactants, buffers, salts, carrier proteins, preservatives and the like.

B. Preparation of Formulations:

The present invention is drawn to non-aqueous formulations of proteinaceous particles and nucleic acid particles with less than about 10% hydration suspended in anhydrous, aprotic, hydrophobic, non-polar vehicles with low reactivity, which formulations are stable for prolonged periods of time, even at elevated temperatures. Standard dilute aqueous peptide and protein formulations require manipulation of buffer type, ionic strength, pH and excipients (e.g., EDTA and ascorbic acid) to achieve stability. Standard nucleic acid formulations require formulation or reconstitution immediately prior to administration. In contrast, the claimed formulations achieve stabilization of protein or nucleic acid compounds by the use of dry particles and hydrophobic, anhydrous, non-polar, aprotic low-reactivity vehicles. In particular, stability and flowability of high concentrations (up to about 30%, w/w) of compound has been provided by the formulations of the present invention.

Examples of proteins and proteinaceous compounds which may be formulated using the present invention include those proteins which have biological activity or which may be used to treat a disease or other pathological condition. They include, but are not limited to growth hormone, Factor VIII, Factor IX and other coagulation factors, chymotrypsin, trypsinogen, alpha-interferon, beta-galactosidase, lactate dehydrogenase, growth factors, clotting factors, enzymes, immune response stimulators, cytokines, lymphokines, interferons, immunoglobulins, interleukins, peptides, somatostatin, somatotropin analogues, somatomedin-C, Gonadotropic releasing hormone, follicle stimulating hormone, luteinizing hormone, LHRH, LHRH analogues such as leuprolide, nafarelin and goserelin, LHRH agonists and antagonists, growth hormone releasing factor, calcitonin, colchicine, gonadotropins such as chorionic gonadotropin, oxytocin, octreotide, somatotropin plus an amino acid, vasopressin, adrenocorticotrophic hormone, epidermal growth factor, prolactin, somatotropin plus a protein, cosyntropin, lypressin, polypeptides such as thyrotropin releasing hormone, thyroid stimulation hormone, secretin, pancreozymin, enkephalin, glucagon, endocrine agents secreted internally and distributed by way of the bloodstream, and the like. Further agents that may be delivered include a, antitrypsin, insulin and other peptide hormones, adrenal cortical stimulating hormone, thyroid stimulating hormone, and other pituitary hormones, interferon α, β, and γ, consensus interferon, erythropoietin, growth factors such as GCSF, GM-CSF, insulin-like growth factor 1, tissue plasminogen activator, CF4, dDAVP, tumor necrosis factor receptor, pancreatic enzymes, lactase, interleukin-1 receptor antagonist, interleukin-2, tumor suppresser proteins, cytotoxic proteins, retroviruses and other viruses, viral proteins, antibodies, recombinant antibodies, antibody fragments and the like.

Examples of nucleic acid compounds which may be formulated using the present invention include those nucleic acids which code for proteins which have biological activity or which may be used to treat a disease or other pathological condition, such as the protein compounds listed above. Nucleic acids, including sense or antisense oligonucleotides, which block or reduce production of unwanted proteins are also useful in the present invention. Also included in nucleic acids which may be used in the present invention are those which, either directly or by coding for a protein, stimulate an animal to produce immunity against a disease condition (e.g., cancer) or infection by a pathogenic organism such as a bacteria, virus or protozoa.

The above agents are useful for the treatment or prevention of a variety of conditions including but not limited to hemophilia and other blood disorders, growth disorders, diabetes, leukemia, hepatitis, renal failure, HIV infection, hereditary diseases such as cerebrosidase deficiency and adenosine deaminase deficiency, hypertension, septic shock, autoimmune diseases such as multiple sclerosis, Graves disease, systemic lupus erythematosus and rheumatoid arthritis, shock and wasting disorders, cystic fibrosis, lactose intolerance, Crohn's disease, inflammatory bowel disease, gastrointestinal and other cancers. Analogs, derivatives, antagonists, agonists and pharmaceutically acceptable salts of the above may also be used.

The protein and nucleic acid compounds useful in the formulations and methods of the present invention can be used in the form of a salt, preferably a pharmaceutically acceptable salt. Useful salts are known to those of skill in the art and include salts with inorganic acids, organic acids, inorganic bases or organic bases. Nucleic acids may also be complexed with lipids or be presented as liposomes, ribozymes, viral vectors, virosomes, dendrimers, cationic polymers, PLGA particles, or the like.

The proportion of protein or nucleic acid may vary depending on the compound, the condition to be treated or prevented, the expected dose and the route and duration of administration. (See, for example, *The Pharmacological Basis of Therareutics*, Gilman et al., 7th ed. (1985) and *Pharmaceutical Sciences*, Remington, 18th ed. (1990), the disclosures of which are incorporated herein by reference.) Applicable routes include oral, enteral, transdermal, percutaneous, parenteral, mucosal and the like, all of which are known to those of skill in the art. The concentration of protein or nucleic acid in high concentration formulations may range from at least about 1% (w/w) up to about 30% while still maintaining flowability. A preferred range for proteins is from about 10% to about 30% (w/w).

The vehicles useful in the present invention are non-aqueous, anhydrous, aprotic, non-polar, hydrophobic vehicles with low reactivity. Such vehicles have a dielectric constant less than or equal to about 15; do not contain acidic hydrogen, i.e., hydrogen attached to an oxygen or nitrogen; and generally do not solubilize or otherwise react with proteinaceous compounds. Preferred vehicles include: a) saturated hydrocarbons, b) halogenated saturated or unsaturated hydrocarbons, and c) esters and ethers of a) or b).

Particularly preferred vehicles are perhalohydrocarbons and unsubstituted saturated hydrocarbons. Most preferred vehicles are biocompatible, such as perfluorodecalin, perflurobutylamine, perfluorotripropylamine, perfluoro-N-methyldecahydroquindine, perfluoro-octohydro quinolidine, perfluoro-N-cyclohexylpyrilidine, perfluoro-N,N-dimethylcyclohexyl methylamine, perfluoro-dimethyl-adamantane, perfluorotri-methylbicyclo (3.3.1) nonane, bis(perfluorohexyl) ethene, bis(perfluorobutyl) ethene, perfluoro-1-butyl-2-hexyl ethene, tetradecane, methoxyflurane or mineral oil.

The proteinaceous or nucleic acid powders useful in the present invention are solid particles wherein the hydration of the particle is less than about 10% (w/w water/compound). In contrast to previous protein formulations, where hydration and flexibility were required in order to maintain enzymatic activity, the proteins of the particles used in the present invention have minimal flexibility and minimal exposure to the degradative effects of moisture since protein hydration is minimized. In contrast to previous nucleic acid formulations, which required hydration in order to administer the formulation, the present formulations reduce hydration and degradation of the nucleic acid compounds while providing a flowable formulation suitable for administration. The powders may be produced by milling, spray drying, spray freeze-drying, lyophilization, precipitation, and the like. These protected powder particulates are preferably prepared using solid processing. They may optionally include protecting agents such as carbohydrates, sucrose, trehalose, sorbitol, raffinose, dextrans or cyclodextrins which may, for example, hydrogen bond to the proteins to reduce their effective hydration. They may also contain bulking agents such as glycine or mannitol that modify the morphology and/or processing characteristics of the proteins or nucleic acids, buffers that modify the pH, and non-ionic surfactants which protect from surface absorption and solubilize the protein or nucleic acids. The formulation of dry protein or nucleic acid powders is well known to those skilled in the art.

Here, protein or nucleic acid hydration refers to the fraction of the total moisture in a powder formulation associated with the protein or nucleic acid. Certain excipients (e.g., carbohydrates) reduce the amount of water associated with proteins [14] or nucleic acids. For purposes of this application, protein or nucleic acid hydration will be equal to the moisture content of the powder (determined, for example, by Karl Fischer analysis), expressed as a percentage, multiplied by the fractional weight of protein or nucleic acid in the powder.

Generally, the stable formulations of the present invention may be prepared by simply suspending the desired amount, which may be a therapeutically effective amount, of the desired proteinaceous or nucleic acid powder in the selected vehicle. Preferred vehicles include MO, PFD, MF, PTA and TD.

C. Methodology:

We have found that stable non-aqueous formulations of protein or nucleic acid compounds may be prepared by suspending dry (less than about 10% hydration) particles containing the protein or nucleic acid compound to be formulated in anhydrous, aprotic, hydrophobic, low-reactivity vehicle.

We have tested these formulations for stability by subjecting them to aging at elevated temperature (37° C.) and measuring the chemical and/or physical stability of the formulations. Results of these studies (shown, for example, in Examples 1, 2 and 3) demonstrate that these formulations were stable for at least one month at 37° C.

A major aspect of the invention is that the flowable non-aqueous formulations of the present invention are chemically and physically stable at high temperatures for long periods of time. Such formulations are stable even when high concentrations are used. Thus, these formulations are advantageous in that they may be shipped and stored at temperatures at or above room temperature for long periods of time. They are also suitable for use in implantable delivery devices.

DISCLOSURE OF EXAMPLES OF THE INVENTION

The following method was used to perform the studies in the Examples that follow.

Karl Fischer Moisture Analysis: Vials and stoppers were dried overnight in a vacuum oven at 80° C. Approximately 6 mg of sample was weighed into a dry vial and the vial was stoppered. Control vials were prepared by simply stoppering an empty dry vial (i.e., a vial containing no sample). Subsequently, 150 μL aliquots of dry methanol was added to sample and control vials via a 250 μL Hamilton Syringe (Hamilton Co., Reno, Nev.) which had been previously washed three times with dry methanol. The vials were then sonicated at room temperature until all solids were dispersed, centrifuged, and 100 μL of the supernatant methanol was injected into an Aquatest 10 Coulometric Moisture Analyzer (SeraDyn Inc., Indianapolis, Ind.). The resultant readings were recorded, and water content of the sample calculated by subtracting the control reading from that of the sample.

The following reagents were used to perform the studies in the Examples that follow.

Perfluorodecalin, perfluorotributylamine and tetradecane were purchased from Aldrich Chemical Company (Milwaukee, Wis.). Methoxyflurane was purchased from Abbott Laboratories (North Chicago, Ill.). Light Mineral Oil USP was purchased from Spectrum Chemical Corp. (Gardena, Calif.).

The following examples are offered to illustrate this invention and are not meant to be construed in any way as limiting the scope of this invention.

EXAMPLE 1

Alpha-Interferon Formulations

Stability of Alpha Interferon (α-IFN) Suspensions

Human recombinant Interferon-α-2a ((α-IFN) (Scitech Genetics Ltd., lot# 036R2801) was formulated as a 5 mg/mL solution containing 5 mM citrate, 0.5% sucrose, and 0.005% Tween 80, pH 4.5. Aliquots of 200 μL of this solution were then dispensed into 1 mL glass lyophilization vials, partially covered with lyophilization stoppers, and lyophilized using an FTS Systems lyophilizer according to the following cycle:
Pre-cool shelves to 5° C.;
Load vials;
Freeze to −50° C. at 2.5° C./min;
When product is at −30° C. set vacuum to 125 mT;
Hold at −50° C. for 30 min;
Ramp to 0° C. at 0.5° C./min;
Hold at 0° C. for 120 min;
Ramp to 20° C. at 1 ° C./min;
Hold at 20° C. for 120 min;
Ramp to 30° C. at 1 ° C./min;
Hold at 20° C. for 1000 min; and
Stopper vials.

The resultant powder had a moisture content of approximately 5% (w/w) as determined by Karl Fischer analysis and a protein hydration of about 2.5%. Suspensions were prepared by adding 100 μL of either perfluorodecalin (PFD), methoxyflurane (MF), or mineral oil (MO) to the vials containing the α-IFN powder, and the vials incubated at 37° C. Samples were pulled at 2 and 4 weeks, and the α-IFN extracted from the non-aqueous phase by adding 700 μL of buffer (containing 5 mM citrate, 0.5% sucrose, and 0.005% Tween 80, pH 4.5) and gently inverting the vials. After 15 minutes, an aliquot of the aqueous phase was removed and analyzed for stability by reverse phase HPLC and reduced and non-reduced SDS-PAGE electrophoresis.

The formulations remained chemically stable as determined by reverse phase HPLC (Table 1). In addition, no aggregation or cleavage products were observed on reduced or non-reduced SDS-PAGE gels.

TABLE 1

Stability of α-IFN suspensions at 37° C. as measured by reverse phase chromatography

| Time (weeks) | % Recovery PFD susp 37° C. | % Recovery MF susp 37° C. | % Recovery MO susp 37° C. |
|---|---|---|---|
| 0 | 98 ± 3 | 92 ± 6 | 101 ± 1 |
| 2 | 103 ± 2 | 81 ± 3 | 94 ± 3 |
| 4 | 98 ± 1 | 81 ± 1 | 84 ± 2 |

*Numbers represent mean ± standard deviation of 2–3 samples

RP-HPLC Instrument: Hewlett Packard HP-1090 Flow Rate: 0.3 mL/min Detection: 210 nm Column: Waters Delta-Pak, c18, 150 × 2 mm, 300Å. Mobile Phase: A = 30/70/0.2 Acetonitrile/Water/TFA B = 80/20/0.2 Acetonitrile/Water/TFA

| Gradient: | |
|---|---|
| Time | % B |
| 0 | 23 |
| 45 | 35 |
| 55 | 52 |
| 60 | 90 |
| 65 | 90 |
| 68 | 23 |

SDS-PAGE Apparatus: Life Technologies Vertical Gel Electrophoresis system. Gel: 15% discontinuous, 15 ×17 cm, 0.8 mm thick. Running Conditions: 200v, 50 mA, approximately 3 hrs. Staining: Coomassie Blue R-250 Gel Analysis: Bio-Rad GS-700 image analyzer with Molecular Analyst software.

EXAMPLE 2

Stability of Chymotrypsin Formulations

Formulations were prepared containing 2% chymotrypsin (Worthington Biochemical Corp., 1×Crystallized, Lot# H5B7405L), determined by Karl Fischer analysis to have a water content and protein hydration of approximately 7% (w/w), either dissolved in 0.1M borate buffer, pH 8.0, or suspended (as a dry powder) in either perfluorodecalin or Light Mineral Oil, U.S.P. Samples were stored at 37° C. for 10 weeks, and assayed for chymotrypsin activity using casein as a substrate.

The results are shown in Table 2 and demonstrate stability of the formulations.

Chymotrypsin Bioactivity assay

Samples were diluted in 0.1 M borate buffer, pH 8.0, such that the final chymotrypsin concentration for assay was approximately 2–50 μg/mL. A casein substrate solution was prepared by suspending 1 gm of casein in 95 mL borate buffer, pH 8.0 and heating in a boiling water bath until the casein had dissolved (approximately 10 minutes), then adding 1.1 mL 5% $CaCl_2$ and diluting the solution to 100 mL with 0.1M borate buffer solution at pH 8.0. The substrate solution (1.0 mL) was prewarmed at 37° C. in a heating block, and to it was added 1.0 mL of the sample. The solutions were mixed and incubated at 37° C. for exactly 20 minutes. Subsequently, 3.0 mL of 5% trichloroacetic acid was added, and the resultant mixture was allowed to stand at room temperature for 30 minutes, then centrifuged for 20 minutes at 3,000 g. The absorbance of the supernatant was read in a UV spectrophotometer at 280 nm and the activity (in Units/mg) calculated by the following equation.

$$\text{Activity} = \frac{A_t}{(C)(t)}$$

where: $A_t$=absorbance of supernatant (at 280 nm) at time t of the reaction (in this case, 20 minutes); C=concentration of chymotrypsin in sample; and t=time of reaction (20 minutes).

TABLE 2

Activity of chymotrypsin formulations when stored at 37° C.

| Time (weeks) | % Remaining PFD* | % Remaining MO* | % Remaining Buffer* |
|---|---|---|---|
| 0 | 103 ± 5 | 100 ± 5 | 100 ± 4 |
| 1 | 97 ± 2 | 86 ± 1 | 23 ± 2 |
| 3 | 102 ± 3 | 96 ± 3 | 19 ± 2 |
| 6 | 102 ± 2 | 89 ± 1 | 22 ± 4 |
| 10 | 102 ± 3 | 92 ± 2 | |

*Numbers represent mean ± standard deviation of 6 samples

EXAMPLE 3

Stability of Plasma of Protin Suspensions

Formulations of a post-translationally modified plasma protein of 55 kilodalton molecular weight were prepared containing 1 mg/mL protein and approximately 30 mglmL excipients, buffered to a neutral pH. One mL aliquots of the above solutions were pipetted into 3 mL glass vials, covered with lyophilization stoppers, loaded into a freeze dry chamber (FTS Systems Inc.), and lyophilized.

The resultant powder had a final moisture content of about 0.25% (w/w) water, as determined by Karl Fischer analysis and protein hydration of about 0.008%. Suspensions were prepared by adding 1 mL of either perfluorodecalin (PFD) or methoxyflurane (MF) to the vials containing the dry protein powder, and the vials were then incubated at 37° C. Control samples of the lyophilized powder were stored at −80° C. Samples were pulled at 0, 4.5, 6.5, 8.5 and 12.5 weeks and analyzed for activity using a bioactivity assay, and for chemical stability by size exclusion chromatography.

The results are summarized in Tables 3 and 4 and show that the formulations remained chemically (as determined by biological activity) and physically (as determined by SEC) stable.

Size Exclusion Chromatography Column: TSD G3000 swxl column, 7.8 × 300 mm, 5 μm (ToSoHaas TO8541 or equivalent) Mobile Phase: 50 mM $Na_2HPO_4$, 150 mM NaCl, pH 7.0 Flow Rate: 1.0 mL/min Detector: 214 nm Injection Volume: 50 μL

TABLE 3

Stability of plasma protein suspensions at 37° C. as measured by bioactivity assay

| Time (weeks) | %LS† Lyo. Powder −80° C. | %LS† PFD susp. 37° C. | %LS† MF susp 37° C. |
|---|---|---|---|
| 0 | 92 ± 14 | 84 ± 14 | 92 ± 4 |
| 1.5 | 98 ± 12 | 109 ± 9 | 107 ± 16 |
| 4.5 | 89 ± 2 | 86 ± 4 | 61 ± 20 |
| 6.5 | 94 ± 7 | 101 ± 0 | 68 ± 15 |
| 8.5 | 110 ± 2 | 97 ± 2 | 62 ± 5 |
| 12.5 | 111 ± 7 | 105 ± 11 | |

†%LS = %Label Strength = $\frac{[\text{protein}]\text{test}}{[\text{protein}]\text{control}}$

*Numbers represent mean ± standard deviation of 3 samples

TABLE 4

Stability of plasma protein suspensions at 37° C. as measured by size exclusion chromatography.

| Time (weeks) | %LS† Lyo. Powder −80° C.* | %LS† PFD susp. 37° C.* | %LS† MF susp 37° C.* |
|---|---|---|---|
| 0 | 92 ± 0 | 96 ± 1 | 84 ± 7 |
| 1.5 | 107 ± 3 | 106 ± 2 | 104 ± 4 |
| 4.5 | 108 ± 2 | 96 ± 1 | 67 ± 35 |
| 6.5 | 113 ± 2 | 101 ± 2 | 79 ± 12 |
| 8.5 | 105 ± 1 | 95 ± 4 | 57 ± 5 |
| 12.5 | 100 ± 3 | 98 ± 1 | |

†%LS = %Label Strength = $\frac{[\text{protein}]\text{test}}{[\text{protein}]\text{control}}$

*Numbers represent mean ± standard deviation of 3 samples

EXAMPLE 4

High Concentration Flowable Formulatiopns

Solutions were prepared containing either Albumin (Sigma, Lot 129F01431), Lysozyme (Sigma Lot 65H7025) or Trypsinogen (Worthington Lot# 38E273N) and sucrose in a 1:1 (w/w) ratio. The solutions were spray dried on a Yamato ADL 31 Spray Dryer (Yamato Corp., N.Y.) with the following parameters: inlet temp 120° C., outlet temperature 65° C., atomizer 1.2 $kg/cm^2$. The powders were then transferred to a vacuum oven and allowed to further dry at 30° C. overnight under full vacuum. The moisture content of the powders studied was approximately 4.5% (w/w) as determined by Karl Fischer analysis with a protein hydration of about 2.25%.

Pastes were formulated by mixing 700 mg of each powder with 1.0 mL of perfluorodecalin (approximately 28% w/w). The pastes were loaded into 1.0 cc syringes fitted with 30 Gauge needles (Becton Dickinson), and extruded. All pastes extruded evenly and completely with little effort.

EXAMPLE 5

Stability of Factor IX Suspensions

Coagulation Factor IX (FIX) from human serum (Calbiochem-Novobiochem, La Jolla, Calif.) was formulated as a 0.5 mg/mL solution containing 60 mg/mL sucrose, 60 mg/mL mannitol, 1 mg/mL polysorbate and 1.6 mg/mL histidine buffer buffered to a pH of approximately 7. One mL aliquots of this solution were lyophilized according to the cycle above. The resultant powder had a moisture content of 1%, as determined by Karl Fischer analysis.

Suspensions were prepared by adding 1 mL of perfluorodecalin (PFD), perfluorotributylamine (PTA) or tetradecane (TD) to the vials containing the dry FIX powder. The vials were incubated at 37° C. Control samples of the lyophilized powder were stored at −80° C. Samples were pulled at 0 and 2 weeks and analyzed for FIX activity by clotting bioactivity assay, and for chemical stability by size exclusion chromatography.

The results (Tables 5 and 6) showed that the formulations remained chemically (as determined by biological activity) and physically (as determined by SEC) stable.

TABLE 5

Stability of Factor IX Suspensions at 37° C. as Measured by Bioactivity Assay

| Time (weeks) | %LS† PFD susp. 37° C. | %LS† PTA susp. 37° C. | %LS† TD susp. 37° C. |
|---|---|---|---|
| 0 | 97 ± 2 | 89 ± 3 | 95 ± 3 |
| 2 | 98 ± 2 | 96 ± 1 | 96 ± 1 |

†%LS = %Label Strength = $\frac{[protein]test}{[protein]control}$

*Numbers represent mean ± standard deviation of 3 samples

TABLE 6

Stability of Factor IX Suspensions at 37° C. as Measured by Size Exclusion Chromatography.

| Time (weeks) | % LS† PFD susp. 37° C. | % LS† PTA susp. 37° C. | % LS† TD susp. 37° C. |
|---|---|---|---|
| 0 | 94 ± 1 | 93 ± 1 | 97 ± 1 |
| 2 | 94 ± 2 | 95 ± 2 | 96 ± 1 |

†% LS = % Label Strength = $\frac{[protein]\ test}{[protein]\ control}$

*Numbers represent mean ± standard deviation of 3 samples

EXAMPLE 6

Stability of Nuclueic Acid Suspensions

Plasmid pCIN.CAT was made by cloning the coding sequence for bacterial chloramphenicol acetyltransferase (CAT) into the expression plasmid pClneo (Promega). The CAT coding region was isolated by PCR amplification from plasmid pSIS.CAT [42] by standard techniques (PCR Technology. 1989. H. A. Erlich, ed. Stockton Press, incorporated herein by reference). These primers produced a unique XhoI restriction site at the 5'-end and a unique NotI restriction site at the 3' end. This fragment was subcloned into the XhoI and NotI sites of pClneo by standard techniques (Molecular Cloning, second edition. 1989. Sambrook, J., Fritsch, E. F., and Maniatis, T., incorporated herein by reference.) Plasmid DNA was grown in bacterial culture and isolated (Qiagen, GmbH).

Formulations were prepared containing 100 mg/ml sucrose, 100 mg/ml mannitol, 10 μg/ml pCIN-CAT DNA, 50 μg/ml of a 1:1 formulation of DOTMA (n-[1-(2,3 dioleyloxy)propyl]-n,n,n-trimethylammoniumchloride) and DOPE (dioleoyl phosphotidylethanolamine) (Lipofection, GIBCO BRL) in 10 mM Tris buffer at pH 7.1. Aliquots of 200 μl of the above formulation were pipetted into 1 ml glass vials and lyophilized using the following protocol:
Precool shelf temperature to 5° C.;
Load vials;
Freeze to −40° C. at 0.4° C./min and hold at −40° C. for 120 minutes;
Ramp to −10° C. at 0.4° C./min and hold for 240 minutes;
Ramp to −45° C. at 0.4° C./min and hold for 120 minutes;
Set vacuum to 100 mT;
Hold at −45° C. for 360 minutes with vacuum at 100 mT;
Ramp to −25° C. at 0.04° C./min with vacuum at 100 mT;
Hold at 25° C. for 1500 minutes with vacuum at 100 mT.

The subsequent dry powder had a moisture content of approximately 2% as measured by Karl Fischer analysis. Suspensions were prepared by adding 300 μl of perfluorodecalin (PFD) to the vials in a glove box under dry nitrogen. Suspension, dry powder and solution samples were incubated at 37° C. for 1, 4 and 7 days, and subsequently monitored for biological activity by monitoring gene transfer efficiency as measured by CAT expression in HEK293 cells. Transfection of HEK 293 cells with lipid/DNA complexes was performed as described by the Manufacturer (GIBCO BRL). The results are shown in Table 7, and demonstrate that when lipid/DNA complexes were formulated in aqueous solution, essentially all activity was lost when the solution was stored at 37° C. for 1 week. In contrast, both the lyophilized dry nucleic acid powder and the nucleic acid powder suspended in PFD retained essentially all their biological activity (within the experimental variability of the assay) when stored for 1 week at 37° C.

TABLE 7

Transfection Activity of Lipid/DNA Constructs After Incubation at 37° C. (Numbers are mean ± standard deviation of 12 replicates.)
Average ng CAT Protein Expressed Per mg Total Cellular Protein

| Time (days) | Solution Formulation | Dry Powder Formulation | PFD Suspension Formulation |
|---|---|---|---|
| 0 | 478 ± 254 | 219 ± 114 | n.d. |
| 1 | 115 ± 46 | 628 ± 192 | 273 ± 122 |
| 4 | 13 ± 12 | 255 ± 137 | 284 ± 267 |
| 7 | 6 ± 3 | 377 ± 202 | 339 ± 151 |

Modification of the above-described modes of carrying out various embodiments of this invention will be apparent to those of skill in the art following the teachings of this invention as set forth herein. The examples described above are not limiting, but are merely exemplary of this invention, the scope of which is defined by the following claims.

What is claimed is:

1. A stable non-aqueous composition of a biologically active agent comprising:
   a) a biologically active agent containing powder wherein the biologically active agent hydration in said powder is less than 10%; and
   b) at least one anhydrous, aprotic, hydrophobic, non-polar, low-reactivity vehicle, wherein at least one said vehicle is selected from the group consisting of perfluorodecalin, methoxyflurane, and perfluorotributylamine, and wherein said biologically active agent is selected from the group consisting of proteins and proteinaceous compounds.

2. The composition of claim 1 wherein at least about 80% of the biologically active agent remains stable for at least one month at 37° C.

3. The composition of claim 1 wherein said biologically active agent hydration is less than about 5%.

4. The composition of claim 1 wherein said biologically active agent containing powder comprises up to about 30% (w/w) of said composition.

5. The composition of claim 1 wherein said biologically active agent is a protein selected from the group consisting of Factor IX, Factor VIII, alpha-interferon, consensus interferon, beta-galactosidase, lactate dehydrogenase, chymotrypsin, an antibody, and analogs thereof.

6. The composition of claim 1 wherein said biologically active agent is pharmaceutically useful.

7. A method for preparing the composition of claim 1 comprising suspending said biologically active agent-containing powder of claim 1 in at least one anhydrous, aprotic, hydrophobic, non-polar, low-reactivity vehicle, wherein at least one said vehicle is selected from the group consisting of perfluorodecalin, methoxyflurane, and perfluorotributylamine.

8. The composition of claim 1 or method of claim 7 wherein said biologically active agent containing powder comprises about 10 to about 30% (w/w) of said composition.

9. A method for administering the biologically active agent according to claim 1 to a subject, said method comprising administering to said subject an effective amount of the composition of claim 1.

10. The method of claim 9 wherein the administration of the composition is via a route selected from the group consisting of parenteral, transdermal, mucosal, oral and enteral.

11. The the method of claim 9 wherein the administration of the composition is via an implantable delivery device.

12. The method of claim 9 wherein the administration of the composition is long-term continuous administration.

* * * * *